US008178501B2

(12) United States Patent
Chaudhary

(10) Patent No.: US 8,178,501 B2
(45) Date of Patent: *May 15, 2012

(54) ANTIBIOTIC COMBINATIONS FOR PROVIDING TOTAL SOLUTION TO THE TREATMENT OF INFECTIONS

(75) Inventor: Manu Chaudhary, Haryana (IN)

(73) Assignee: Venus Remedies Limited, Panchkula-Haryana (IN)

( * ) Notice: Subject to any disclaimer, the term of this patent is extended or adjusted under 35 U.S.C. 154(b) by 501 days.

This patent is subject to a terminal disclaimer.

(21) Appl. No.: 11/721,837

(22) PCT Filed: Dec. 16, 2005

(86) PCT No.: PCT/IN2005/000415
§ 371 (c)(1),
(2), (4) Date: Jun. 15, 2007

(87) PCT Pub. No.: WO2006/064516
PCT Pub. Date: Jun. 22, 2006

(65) Prior Publication Data
US 2009/0318378 A1 Dec. 24, 2009

(30) Foreign Application Priority Data
Dec. 17, 2004 (IN) .......................... 2510/DEL/2004

(51) Int. Cl.
A61K 31/7016 (2006.01)
A61P 31/04 (2006.01)

(52) U.S. Cl. ....................................... 514/36
(58) Field of Classification Search ........................ None
See application file for complete search history.

(56) References Cited

U.S. PATENT DOCUMENTS

| 4,263,280 | A | | 4/1981 | Kradolfer et al. | |
|---|---|---|---|---|---|
| 4,775,533 | A | * | 10/1988 | Grab | 424/451 |
| 5,217,493 | A | | 6/1993 | Raad et al. | |
| 5,641,514 | A | | 6/1997 | Cho et al. | |
| 5,795,563 | A | | 8/1998 | Kallick et al. | |
| 6,087,123 | A | * | 7/2000 | Wissler et al. | 435/69.1 |
| 6,900,184 | B2 | * | 5/2005 | Cohen et al. | 514/36 |
| 2003/0055022 | A1 | | 3/2003 | Bonner et al. | |
| 2003/0186957 | A1 | * | 10/2003 | Blanchflower et al. | 514/202 |

FOREIGN PATENT DOCUMENTS

| FR | 2546406 A | 11/1984 |
|---|---|---|
| WO | 01/34128 A2 | 5/2001 |
| WO | 03/082248 A | 10/2003 |

OTHER PUBLICATIONS

Gould, G. W.,British Medical Bulletin, "Preservation: past, present and future", 2000, vol. 56, No. 1, pp. 84-96.*
Wright, D. N. et al., Archives of Pathology & Laboratory Medicine, "In vitro inactivation of aminoglycosides by cephalosporin antibiotics", May 1988, vol. 112, issue 5, pp. 526-528.*
Plager, Association of Renal Injury with Combined Cephalothin-Gentamicin Therapy Among Patients Severely Ill with Malignant Disease, Cancer, Apr. 1976, p. 1937-1943, vol. 37, No. 4, Wiley, USA.
Hughes, et al., 1997 Guidelines for the Use of Antimicrobial Agents in Neutropenic Patients with Unexplained Fever, Clinical Infectious Diseases, 1997, p. 551-573, vol. 25, No. 3, The University of Chicago Press, USA.
Charnas, et al., Once Daily Ceftriaxone Plus Amikacin v. Three Times Daily Ceftazidime Plus Amikacin for Treatment of Febrile Neutropenic Children with Cancer, The Pediatric Infectious Disease Journal, Apr. 1997, p. 346-353, vol. 16, No. 4, Lippincott Williams & Wilkins, USA.
Freifeld, et al., Use of Fluoroquinolones for Empirical Management of Febrile Neutropenia in Pediatric Cancer Patients, The Pediatric Infectious Disease Journal, Jan. 1997, p. 140-146, vol. 16, No. 4, Lippincott Williams & Wilkins, USA.
Patrick, Viridans Streptococcal Infections in Patients with Neutropenia, The Pediatric Infectious Disease Journal, Mar. 1999, p. 280-281, vol. 18, No. 3, Lippincott Williams & Wilkins, USA.
Schimpff,et al., Empiric Therapy with Carbenicillin and Gentamicin for Febrile Patients with Cancer and Granulocytopenia, The New England Journal of Medicine, May 1971, p. 1061-1065, vol. 284, No. 19, Massachusetts Medical Society, USA.
Cometta, et al., Piperacillin-Tazobactam plus Amikacin versus Ceftazidime plus Amikacin as Empiric Therapy for Fever in Granulocytopenic Patients with Cancer, Antimicrobial Agents and Chemotherapy, Feb. 1995, p. 445-452, vol. 39, No. 2, American Society for Microbiology, USA.

(Continued)

Primary Examiner — Shaojia Anna Jiang
Assistant Examiner — Bahar Schmidtmann
(74) Attorney, Agent, or Firm — Hultquist, PLLC; David S. Bradin; Steven J. Hultquist

(57) ABSTRACT

The invention relates to a new pharmaceutical composition, a method of treatment of infection and also a process to prepare the composition. The infectious complications are important causes of morbidity and mortality. Hospital acquired pneumonia (HAP) remains the most severe nosocomial infection in intensive care units. Beta-lactams alone are always considered inadequate when *P. aeruginosa* and/or methicillin-resistant *S. aureus* are implicated as pathogens or copathognes. The present invention provides the desired empirical therapy for control of all bacterial infections. The invention provides antibiotic combination products for delivering at least two different antibiotics, through parenteral dosage form comprising protein-synthesis-inhibiting antibiotic which is amikacin or its sulphate salt and non-protein-synthesis-inhibiting antibiotic which is cefepime or its hydrochloride salt. The invention provides a total solution, against multiresistant *P. aeruginosa*, or Acinetobacter spp. and/or methicillin-resistant *S. aureus*, and are useful for intramuscular or intravenous administration as antibiotics for hospitalized patients with acute or serious infections. The pharmaceutical compositions described here normally have the least nephrotoxicity and have better efficacy and safety of cefepime plus amikacin combination.

13 Claims, No Drawings

OTHER PUBLICATIONS

Chudanova, et al., Cefepime/amikacin in the empirical antibacterial therapy for patients with hemoblastosis of different forms, Antibiotiki i khimioterapiia, 2003, p. 29-32, vol. 48, No. 7, Izdatelstvo Medisina, Russia. (English Abstract Only).

Barbhaiya R H et al., Lack of Pharmacokinetic Interaction Between Cefepime and Amikacin in Humans, Antimicrobial Agents and Chemotherapy, 1992, p. 1382-1386, vol. 36, No. 7.

Cordonnier C et al., Cefepime/amikacin versus ceftazidime/amikacin as empirical therapy for febrile episodes in neutropenic patients: a comparative study, Clinical Infectious Diseases: An Official Publication of the Infectious Diseases Society of America, Jan. 1997, p. 41-51, vol. 24, No. 1.

Sanz Miguel A et al., Cefepime plus amikacin versus piperacillin-tazobactum plus amikacin for initial antibiotic therapy in haematology patients with febrile neutropenia: Results of an open, randomized, multicentre trial, Journal of Antimicrobial Chemotherapy, Jul. 2002, p. 79-88, vol. 50, No. 1.

Beaucaire G et al., Phare Study. Comparative study of the association cefepime-amikacin versus the association ceftazidime-amikacin in the treatment of nosocomial pneumonias in ventilated patients, Annales Francaises D'Anesthesie et de Reanimation, Feb. 1999, p. 186-195, vol. 18, No. 2.

Ford C W et al., In Vivo Activities of U-100592 and 1-100466, Novel Oxazolidinone Antimicrobial Agents, Against Experimental Bacterial Infections, Antimicrobial Agents and Chemotherapy, Jun. 1, 1996, p. 1508-1513, vol. 40, No. 6.

Bui Khanh Q et al., In Vitro and In Vivo Influence of Adjunct Clarithromycin on the Treatment of Mucoid *Pseudomonas aeruginosa*, Journal of Antimicrobial Chemotherapy, Jan. 2000, p. 57-62, vol. 45, No. 1.

* cited by examiner

ANTIBIOTIC COMBINATIONS FOR PROVIDING TOTAL SOLUTION TO THE TREATMENT OF INFECTIONS

FIELD OF THE INVENTION

The invention relates to antibiotic combination products for delivering at least two different antibiotics, wherein the products are comprised of parenteral dosage form and the two different antibiotics comprise at least one protein synthesis inhibiting antibiotic and at least one non-protein synthesis inhibiting antibiotic/bacterial cell wall synthesis inhibiting antibiotic, where in the first antibiotic amikacin present as sulphate can act synergistically with cefepime present as hydrochloride to provide a total solution against multiresistant *P. aeruginosa*, or *Acinetobacter* spp. and/or methicillin-resistant *S. aureus* are useful for intramuscular or intravenous administration as antibiotics for hospitalized patients with acute or serious infections. The pharmaceutical compositions described herein normally have the least nephrotoxicity and have better efficacy and safety of amikacin plus cefepime combination.

BACKGROUND OF THE INVENTION

Cephalosporins are one of the mainstays of antibiotic therapy, and third-generation cephalosporins are first-line agents for the treatment of many types of serious infections, including those of nosocomial origin. Gaps in activity of currently available third-generation cephalosporins such as cefotaxime, cefoperazone, ceftriaxone, and ceftazidime, and increasing reports of gram-negative bacilli resistance to some of these agents, especially *Klebsiella pneumoniae*, *Pseudomonas aeruginosa*, and *Enterobacter* spp., make it necessary to investigate new compounds. Ceftazidime is a commonly prescribed third-generation cephalosporin used for empiric treatment of serious infections such as pneumonia, urinary tract infection, and skin and skin-structure infection but is found to be less effective alone and to develop resistance easily. Cefepime, a fourth-generation cephalosporin with a wide range of activity against grain-positive and gram-negative bacteria, including multi-resistant strains of enterobacteriaceae, is the drug of choice but has limited use due to multiresistant *P. aeruginosa* or *Acinetobacter* supp. and/or methicillin-resistant *S. aureus*. Hence, a combination of fourth generation cephalosporin along with aminoglycoside is required which has less toxicity and maximum compatibility as in the present invention.

The nephrotoxic effects of aminoglycosides (particularly gentamicin and tobramycin) can be increased by the concurrent use of cephalosporins (particularly cefalotin [or cephalothin]). However some cephalosporins (cefuroxime, cefotaxime, ceftazidime and cefipime) appear not to interact adversely. (Plager J E., Cancer 1976; 37: 1937-43). In present invention amikacin is used in combination with cefepime which has lesser nephrotoxicity as compared to other combinations. (Barbhaiya R H et al. Antimicrob Agents in Chemother 1992; 36: 1382-6)

Febrile neutropenia is a common consequence of anticancer chemotherapy with a neutrophil count of less than 500 cells/cubic mm (Hughes et al, 1997, level 2). Cancer patients receiving myelosuppressive chemotherapy develop severe neutropenia and are at a high risk of developing life-threatening infections (Charnas, Luthi & Ruch, 1997, level 1; Cometta et al, 1996). Bacterial infections are a common cause of morbidity and mortality in neutropenic cancer patients (Freifeld & Pizzo, 1997, level 9), with a microbiologic cause for the febrile episode being demonstrated in approximately 40% cases (Charnas, Luthi & Ruch, 1997, level 1). These patients are at risk of *Enterobacteriaceae*, *Klebsiella pneumoniae*, *Staphylococcus aureus*, *Staphylococcus epidermidis* and *viridans streptococci* infections (Charnas, Luthi & Ruch, 1997, level 1; Patrick, 1997). Since febrile neutropenic patients fail to mount a full inflammatory response, and the current diagnostic tests are not sufficiently rapid, sensitive or specific for identifying or excluding the microbial cause of a febrile episode, they may have to treated empirically. The prompt institution of present invention as suitable antibiotic therapy for febrile neutropenic patients, without waiting 24 to 48 hours for the results of blood cultures, dramatically reduces infection-related morbidity and mortality in the cancer population undergoing chemotherapy.

Hospital-acquired pneumonia (HAP) remains the most severe nosocomial infection in intensive care units (ICUs). Some factors influencing mortality have been identified. Bacteraemia and *Pseudomonas aeruginosa* or *Acinetobacter* spp. as causative agents increase mortality. Beta-lactams alone were always considered inadequate when *P. aeruginosa* and/or methicillin-resistant *S. aureus* were implicated as pathogen(s) or copathogen(s).

Treatment instituted before knowing the aetiology and antimicrobial sensitivities is empirical. Therefore, present invention provides the desired empirical therapy for control of these bacterial infections in HAP patients.

Infectious complications are an important cause of morbidity and mortality, especially in patients with cancer with profound and prolonged neutropenia following intensive chemotherapy for haematological malignancies. Thus, prompt administration of empirical broad-spectrum antibiotics at the onset of fever in neutropenic patients with cancer has been the standard care since the 1971 report by Schimpff et al; (New England Journal of Medicine 284, 1061-5) documenting reduction in mortality rates. Combination therapy with an aminoglycoside plus an anti-pseudomonal β-lactam has commonly been recommended because this approach provides broad-spectrum coverage, bactericidal activity and potential synergic effects, and minimizes the development of resistance during treatment. Piperacillin-tazobactam and ceftazidime have been used in combination with aminoglycoside like gentamycin and tobramycin, having nephrotoxicity and lesser efficacy in certain cases. The present invention provides a cutting edge over conventional therapies. (Cometta, A., Zinner, S., De Bock, R., Calandra, T., Gaya, H., Klastersky, J. et al. (1995)Antimicrobial Agents and Chemotherapy 39, 445-52).

Beaucaire G et al. 1999 in Ann Fr Anesth Reanim; February; 18(2):186-95 had studied comparison of cefepime (2 g×2/day)+amikacin (7.5 mg.kg-1×2/day)(=cefe-ami) and ceftazidime (2 g×3/day)+amikacin (7.5 mg.kg-1×2/day) (=cefta-ami) in patients under mechanical ventilation suffering from a nosocomial pneumonia. The efficacy rates of cefe-ami and cefta-ami combinations were similar in ICU patients under mechanical ventilation with a nosocomial pneumonia. However the cefe-ami association was significantly more efficient in the population with a bacteriologically documented pneumonia. Chudanova TV et. Al 2003; Antibiot Khimioter.; 48(7):29-32 studied the results of the use of cefepime (Maxipime) combination with amikacin vs ceftriaxon combination with amikacin in the treatment of 80 patients with different forms of hemoblastosis are presented. They found that the average period of the treatment with cefepime and amikacin equaled to 13 days (8 to 16). The treatment with cefepime+amikacin was successful in 38 out of 40 patients (95%). The average period of the treatment with ceftriaxon and amikacin equaled to 14 days (7 to 18). The efficacy of the treatment with ceftriaxon+amikacin was 60% (24 patients out of 40).

Miguel A. Sanz et al for the Spanish PETHEMA Group 2002. J Antimicrob Chemother. July; 50(1):79-88. In this prospective multicentre trial, 969 patients with 984 febrile neutropenic episodes were randomized to receive iv amikacin (20 mg/kg every 24 h) combined with either cefepime (2 g every 8 h) or piperacillin-tazobactam (4 g/500 mg every 6 h). Clinical response was determined at 72 h and at completion of therapy. Drug-related adverse events were reported in 10% of cefepime plus amikacin versus 11% of piperacillin-tazobactam plus amikacin patients. Mortality due to infection occurred in a total of 10 patients (two cefepime, eight piperacillin-tazobactam).

Similarly Barbhaiya R H, et al. in their paper "Lack of pharmacokinetic interaction between Cefepime and Amikacin in Humans" (Antimicrobial Agents and Chemotherapy, July 1992, pp 1382-6), and Sanz, Miguel A, et al in their paper "Cefepime plus amikacin versus piperacillin-tazobactam plus amikacin . . . "(antimicrobial agents and Chemotherapy, 2002, pp 79-88 have mentioned about use of cefepime and amikacin co-administration.

Co-administering as mentioned in the prior art has a number of disadvantages as stated here:
A) Drugs mentioned as the combinations are administered one after the other.
B) These drugs are not available in a premixed combination. Moreover, one of the drug component is available as liquid (ready to use) and other as dry powder for injection.
C) There is complexity involved in administration of the drug as more number of pricks are required and the time of administration is also long.
D) The chances of nephrotoxicity increases in the case of excess administration of aminoglycoside.

Some other shortcomings of individual administration or co-administration of amikacin and cefepime as done in the prior art are:
a) Treatment time is prolonged to about 20 days in case of individual administration of these drugs and to about 13 days in case of co-administration.
b) Cost to the patient is higher due to increased hospitalization time.
c) The failure rate is higher due to inconsistency of dose. Like Beaucaire G et al. 1999 used cefepime (2 g×2/day)+amikacin (7.5 mg.kg-1×2/day) where as amikacin (20 mg/kg every 24 h) combined with either cefepime (2 g every 8 h) was used by Miguel A. Sanz et al. 2002.

The individual administration of the amikacin and cefepime components of drugs described in the prior art fails to solve the treatment problem satisfactorily because of following reasons:
a) The components are administered one after the other and individually in different doses.
b) The components are administered either in equal proportions or the ratio is undefined and not fixed.
c) The success rate of such a treatment is not as per the desired levels.

Also, adequate dose is not available to the patient and the chances of development of resistance increases in the case of prior art.

It is therefore submitted that the prior art does not address typical problems to which solutions are provided by the present invention.

The individual doses of amikacin and cefepime of prior art for their defined treatment time, are costlier than the combination of present invention. A working on the cost comparison is provided for reference.

Accordingly, there is a need to provide a total solution by providing a pharmaceutical composition of antibiotic composition useful for intramuscular and/or intravenous administration for hospitalization patients with acute or serious bacterial infections, particularly against multiresistant *P. aeruginosa*, or *Acinetobacter* supp. and/or methicillin-resistant *S. aureus*.

OBJECTS AND ADVANTAGES OF INVENTION

Accordingly, the objects and advantages of the present invention are described below:

An object of the present invention is to provide an antibiotic combination product effective against acute/serious bacterial infections.

Another object of the present invention is to provide pharmaceutical compositions having better efficacy and safety.

Yet another object of the present invention is to provide a pharmaceutical composition having the least nephrotoxicity.

Further object of the present invention is to provide pharmaceutically effective dose for intramuscular and/or intravenous administration for hospitalized patients with acute or serious infections.

Another object of the present invention is to reduce hospitalization time.

Yet another object of the present invention to reduce treatment cost to patient

Other objects and advantages of the present invention will become apparent from the ensuing detailed description of the invention.

SUMMARY OF THE INVENTION

The invention relates to a new pharmaceutical composition, a method of treatment of infection and also a process to prepare the composition. The infectious complications are important causes of morbidity and mortality. Hospital acquired pneumonia (HAP) remains the most severe nosocomial infection in intensive care units. Beta-lactams alone are always considered inadequate when *P. aeruginosa* and/or methicillin-resistant *S. aureus* are implicated as pathogens or copathognes. The present invention provides the desired empirical therapy for control of all bacterial infections. The invention provides antibiotic combination products for delivering at least two different antibiotics, through parenteral dosage form comprising protein-synthesis-inhibiting antibiotic which is amikacin or its sulphate salt and non-protein-synthesis-inhibiting antibiotic which is cefepime or its hydrochloride salt. The invention provides a total solution, against multiresistant *P. aeruginosa*, or *Acinetobacter* spp. and/or methicillin-resistant *S. aureus*, and are useful for intramuscular or intravenous administration as antibiotics for hospitalized patients with acute or serious infections. The pharmaceutical compositions described here normally have the least nephrotoxicity and have better efficacy and safety of cefepime plus amikacin combination.

DESCRIPTION OF INVENTION

This invention relates to antibiotic compositions and the uses thereof. More particularly, this invention relates to a composition for the parenteral delivery of two different antibiotics, and the uses of combination thereof.

In many cases, it is desirable to employ two different antibiotics in the treatment of a bacterial infection, in that such antibiotics may have complementary mechanisms of action that facilitate broad-spectrum coverage, bactericidal activity and potential synergistic effects, and to minimize the development of resistance during treatment of the severe or acute bacterial infections.

The terminology "protein synthesis inhibiting antibiotic" means an agent that disrupts the bacterial ribosome cycle through which polypeptide chain initiation and elongation is normally effected. There are multiple points in the ribosome cycle at which this can occur.

The terminology "non-protein synthesis inhibiting antibiotic" means antibiotics other than protein synthesis inhibiting antibiotics.

As non-limiting representative examples of "protein synthesis inhibiting antibiotics" there may be mentioned: the aminoglycosides such as streptomycin, amikacin, netilmicin and tobramycin; the macrolides such as erythromycin and lincomycin; the tetracyclines such as tetracycline, doxycycline, chlortetracycline, and minocycline; the oxalidinones such as linezolid; fusidic acid; and chloramphenicol.

As non-limiting representative examples of "non-protein synthesis inhibiting antibiotics", there may be mentioned: the beta-lactam penicillins such as penicillin, dicloxacillin, and ampicillin; the beta lactam cephalsporins such as cefepime, ceftazidime, cefotaxime, cefuroxime, cefaclor, and ceftriaxone; the beta lactam carbapenems such as imipenem and meropenem; the quinolones such as ciprofloxacin, moxifloxacin, and levofloxacin; the sulfonamides such as sulfanilamide and sulfamethoxazole; metronidazole; rifampin; vancomycin; and nitrofurantoin.

The antibiotics may be in the form of a pharmaceutically acceptable salt. Pharmaceutically acceptable salts means which can be generally used as salts of an antibiotic in pharmaceutical industry, including for example, salts of sodium, potassium, calcium and the like, and amine salts of procaine, dibenzylamine, ethylenediamine, ethanolamine, methylglucamine, taurine, and the like, as well as acid addition salts such as hydrochlorides, and basic amino acids and the like.

The different embodiments of the present invention are described below in details.

This invention basically provides an antibiotic combination for providing total solution to the treatment of infections, where said combination is pharmaceutically acceptable, comprising:
a) first antibiotic and second antibiotic, wherein said first antibiotic is protein-synthesis-inhibiting antibiotic and said second antibiotic is non-protein-synthesis-inhibiting antibiotic;
b) said combination further comprising a stabilizing agent.

In this antibiotic combination, said first antibiotic is selected from the group consisting of the aminoglycosides such as gentamycin, kanamycin, netilmicin, streptomycin, amikacin and tobramycin; and the macrolides such as erythromycin and lincomycin; and the tetracyclines such as tetracycline, doxycycline, chlortetracycline, and minocycline; and the oxalidinones such as linezoloid; and fusidic acid; and chloramphenicol.

In this antibiotic combination said first antibiotic is preferably aminoglycoside, which is selected from the group consisting of gentamycin, amikacin, tobramycin, kanamycin, and netilmicin, or a pharmaceutically acceptable salt of any of these, more preferably amikacin or a pharmaceutically acceptable salt thereof.

In this antibiotic combination said pharmaceutically acceptable salt of amikacin is sulphate salt, that is amikacin sulphate. Amikacin sulfate is a semi-synthetic aminoglycoside antibiotic derived from kanamycin, having a chemical name D-Streptamine, O-3-amino-3-deoxy-α-d-glucopyranosyl)1→6)-O-[6-amino-6-deoxy-α-D-glucopyranosyl(1→4)]-N$^1$-(4-amino-2-hydroxy-1-oxobutyl)-2-deoxy-,(S)-,sulfate (1:2)(salt), and has the molecular formula $C_{22}H_{43}N_5O_{13}.2H_2SO_4$ with a molecular weight of 781.76.

In this antibiotic combination, said second antibiotic is selected from the group consisting of the beta-lactam penicillins such as penicillin, dicloxacillin, and ampicillin; the beta lactam cephalsporins such as cefepime, ceftazidime, cefotaxime, cefuroxime, cefaclor, and cetriaxone; the beta lactam carbapenems such as imipenem and meropenem; the quinolones such as ciprofloxacin, moxifloxacin, and levofloxacin; the sulfonamides such as sulfanilimide and sulfamethoxazole; metronidazole; rifampin; vancomycin; and nitrofurantoin.

In this antibiotic combination said beta-lactam cephalosporin is preferably cefepime, more preferably pharmaceutically acceptable salt of cefepime such as hydrochloride salt of cefepime, that is cefepime hydrochloride. Cefepime hydrochloride is a semi-synthetic, broad spectrum, cephalosporin antibiotic for parenteral administration, has a chemical name 1-[[(6R,7R)-7-[2-(2-amino-4-thiazolyl)-glyoxylamido]-2-carboxy-8-oxo-5-thia-1-azabicyclo[4.2.0]oct-2-en-3-yl]methyl]-1-methyl-pyrrolidinium chloride, 7$^2$-(Z)-(O-methyloxime), monohydrochloride, monohydrate, and which is a white to pale yellow powder with a molecular formula of $C_{19}H_{25}ClN_6O_5S_2.HCl.H_2O$ and a molecular weight of 571.5 and is highly soluble in water.

In this antibiotic combination, the weight ratio of said first antibiotic to said second antibiotic is in the range from about 1:5 to about 5:1, preferably from about 1:4 to about 4:1, more preferably from about 1:3 to about 3:1.

The antibiotic combination of this invention further comprises a stabilizing agent such as 1-arginine wherein the weight of 1-arginine, is in the range of about 35% to about 75% of the combined weight of said first antibiotic and second antibiotic.

In this said antibiotic combination, the dosage form is a parenteral dosage form. The total said dosage is administered preferably twice a day to a patient, spread over a period of 12 hours in a day depending upon the patient condition and severity of infection.

In this antibiotic combination said first antibiotic and said second antibiotic, when released from said parenteral dosage form, reach the maximum serum concentration almost simultaneously with the release.

Alternatively in this antibiotic combination, said first antibiotic and said second antibiotic, when released from said parenteral dosage form, reach the maximum serum concentration in the time-range from about 30 minutes to about 180 minutes, preferably from about 30 minutes to about 90 minutes.

An embodiment of the present invention includes an antibiotic combination, wherein
(a) said first antibiotic is amikacin or a pharmaceutically acceptable salt thereof, which is present in an amount in the range from about 50 mg to about 75 mg, calculated as amikacin free acid;
(b) said second antibiotic is cefepime or a pharmaceutically acceptable salt thereof, which is present in an amount in the range from about 250 mg to about 500 mg, calculated as cefepime free acid; and
(c) said composition further comprising 1-arginine as stabilizing agent, which is present in an amount in the range from about 75 mg to about 150 mg; and wherein said antibiotic combination is reconstituted with 3 ml of water for injection.

Another embodiment of the present invention includes an antibiotic combination, wherein (a) said first antibiotic is amikacin or a pharmaceutically acceptable salt thereof, which is present in an amount in the range from about 100 mg to about 150 mg, calculated as amikacin free acid;
(b) said second antibiotic is cefepime or a pharmaceutically acceptable salt thereof, which is present in an amount in the range from about 500 mg to about 1 g, calculated as cefepime free acid; and
(c) said composition further comprising 1-arginine as stabilizing agent, which is present in an amount in the range from about 150 mg to about 300 mg; and wherein said antibiotic combination is reconstituted with 5 ml of water for injection.

Yet another embodiment of the present invention includes an antibiotic combination, wherein
a) said first antibiotic is amikacin or a pharmaceutically acceptable salt thereof, which is present in an amount in the range from about 200 mg to about 300 mg, calculated as amikacin free acid;
b) said second antibiotic is cefepime or a pharmaceutically acceptable salt thereof, which is present in an amount in the range from about 1 g to about 2 g, calculated as cefepime free acid; and
c) said composition further comprising 1-arginine as stabilizing agent, which is present in an amount in the range from about 300 mg to about 600 mg; and wherein said antibiotic combination is reconstituted with 10 ml of water for injection.

Still another embodiment of the present invention includes an antibiotic combination, wherein
a) said first antibiotic is amikacin or a pharmaceutically acceptable salt thereof, which is present in an amount of about 400 mg to 600 mg, calculated as amikacin free acid;
b) said second antibiotic is cefepime or a pharmaceutically acceptable salt thereof, which is present in an amount of about 2 g to 4 g, calculated as cefepime free acid; and
c) said composition further comprising 1-arginine as stabilizing agent, which is present in an amount of about 600 mg to 1.2 g; and wherein said antibiotic combination is reconstituted with from about 20 ml of water for injection.

In the present invention, a pharmaceutically effective unit dose of said antibiotic combination, in the form of the concentrate of said dose, is provided in a sealed airtight container which is selected from the group consisting of a vial, a mono vial, an ampoule, a syringe, a packet, a pouch and an auto-injector, wherein said container has a head space volume sufficient for introduction of appropriate volume of an aqueous solvent sufficient to form a unit/multiple dose in the form of an appropriate reconstituted solution of said antibiotic combination.

In the present invention, said antibiotic combination is provided in the form of a dry sterilized powder, in a sealed airtight container to form a pharmaceutically acceptable required fixed dose combination for reconstitution prior to intramuscular or intravenous administration for the treatment of the acute or serious bacterial infections. The combination dosage form after reconstitution is a sterile, colorless to light straw colored solution with the pH of the constituted solution being in the range from about 3.5 to about 6.5.

In the present invention, the antibiotic combination is alternatively provided in a sealed container such as transparent glass vial capped with appropriate halogenated stopper and seal, and is used for reconstitution for intramuscular or intravenous administration for the treatment of acute or serious bacterial infections.

Regarding the fill volume of the sealed airtight container, the antibiotic combination of present invention is provided in a reconstituted form in a sealed airtight container which is selected from the group consisting of a vial, a mono vial, an ampoule, a syringe, a packet, a pouch and an auto-injector, wherein interior space of said container comprises a fill volume occupied by said composition in reconstituted form and a head space volume occupied aseptically by an inert-gas-limited microatmosphere, which comprises essentially one or more inert gas which is selected from the group of noble gases and nitrogen; preferably nitrogen, volume of said nitrogen gas being not more than 5% of said head space volume, and wherein ratio of said fill volume to said head space volume is not less than 1:1.

In the present invention of the antibiotic combination, said amikacin or said pharmaceutically acceptable salt thereof, and said cefepime or said pharmaceutically acceptable salt thereof, are present in pharmaceutically effective total amount corresponding to a single unit/multiple dose, in said sealed container, filled aseptically under inert gas blanket.

A method of treating a subject, having a condition or disorder, wherein a treatment with amikacin or a pharmaceutically acceptable salt thereof and cefepime or a pharmaceutically acceptable salt thereof, is indicated, which method comprises parenterally administering therapeutically effective amount of the combination of these two antibiotics to mammals.

An embodiment of the present invention includes a process for preparing an antibiotic combination for providing total solution to the treatment of acute or serious bacterial infections, comprising the steps of:
(a) sterile filling/blending first and second active ingredients, wherein said first active ingredient comprises a first antibiotic which is amikacin or a pharmaceutically acceptable salt thereof, preferably sulphate salt; and wherein said second ingredient is a second antibiotic which is cefepime or a pharmaceutically acceptable salt thereof, preferably cefepime hydrochloride,
(b) sterile adding/blending a stabilizing agent such as 1-arginine, wherein the weight of said 1-arginine is in the range of about 35% to about 75% of the combined weight of said first antibiotic and said second antibiotic,
(c) continuing said sterile blending for a period ranging from about 1 hour to about 4 hours;
(d) proportioning the sterile fill/blend of step (a) to get desired pharmaceutically effective dose in weight ratio of said first active ingredient to said second active ingredient in the range from about 1:5 to about 5:1, preferably from about 1:4 to about 4:1, more preferably from about 1:3 to about 3:1, and.
(e) capping aseptically with pre-post inert gassing.

In accordance with one preferred embodiment of the invention, the average period of the treatment with amikacin and cefepime equaled to 9 days (8 to 10). The treatment with amikacin and cefepime is successful in more than 95% patients.

In general, the invention is available as sterile fill/blend of two or more dry powders to be reconstituted before injection with suitable solvent.

In a preferred embodiment, the antibiotic product is preferably twice a day product, wherein the administration of the antibiotic product is a concentrate which is diluted before administration in suitable infusions; such as 0.9% Sodium Chloride, 5% Dextrose Injection, 0.5% or 1.0% Lidocaine Hydrochloride, or Sterile Bacteriostatic Water for Injection with Parabens or Benzyl Alcohol. The preferred regimen is that the product is administered twice over a twelve hour period depending upon the patient condition and severity of infection.

One of the key features of the present invention is that both the cefepime and amikacin exist in dry powder form along with a stabilizing agent. The combination is a single product as compared to the prior art which already states about co-administration of two different injection, that is cefepime available as dry powder injection and amikacin available as liquid ready to use injection.

A novel feature of the present invention is the combination of amikacin and cefepime which is being used as a predetermined ratio for the first time. The stability has been worked out. A separate accelerated stability report is being attached for the reference.

Another novel feature of the present invention is that by using the combination of amikacin and cefepime, the duration of treatment of a patient is reduced thereby reducing hospitalization time of patients. Moreover, it increases turnover per bed in hospitals as more number of patients can be treated in same duration.

It has also been observed by the inventor that the combination of amikacin and cefepime of the present invention has higher rate of success than the administration of the components of the combination individually. Results of comparative susceptibility studies are provided.

It has further been observed by the inventor that there is no organ deformity or toxicity reported after administration of the dose of the present invention. Reference data is provided.

A part of product development data is provided in support of better efficacy against some of the bacterial range. Experimental study details are given in connection with the present invention in tables 1 to 12.

Bacterial Susceptibility Test:

Bacterial Susceptibility Test was performed for amikacin and cefepime with the Batch No. RTA02. The combination of amikacin and cefepime on different microorganisms was taken to analyze the efficiency of combination in comparison with the individual components of the drug. Different concentrations were selected mentioned to as highest, high, low and lowest in the data. Zone size was determined in mm. The activity of amikacin and cefepime is best seen in *E. coli, Klebsiella pneumoniae, Streptococcus pneumoniae, Enterococcus faecalis, Pseudomonas auriginosa, Staphylococcus aureus*. It was found that the combination works better than the individual components.

Ratio determining Test:

Ratio determining Test was performed for amikacin and cefepime with the Batch No. RTA02. The different ratio of amikacin and cefepime on different microorganisms was taken. Bacterial Lytic Zones for different ratios were determined in mm. The quantity of amikacin and cefepime was taken to be 20 mcg. Bacterial Lytic Zone was best determined in the combination of Amikacin Cefepime taken in 1:4 ratio.

Stability Tests:

The accelerated stability tests were carried out on amikacin and cefepime combination for a duration of six months. The combination was found to be stable.

Toxicity Tests:

Animal behaviour, acute and sub acute toxicity tests were carried out on rodents. A combination dose up to 30 times higher than proposed human dose was given to the experimental animals. The combination in the proposed dose was found to be non toxic.

TABLE 1

Bacterial Susceptibility Data, Amikacin Cefepime, Batch No. RTA02 Amikacin Cefepime Combination on *E. coli*

| Concentration | Cefepime Zone (mm) | Amikacin Zone (mm) | Combination Zone (mm) |
| --- | --- | --- | --- |
| Highest | 32.24 | 30.90 | 32.85 |
| High | 30.16 | 29.02 | 31.12 |
| Low | 24.20 | 22.06 | 24.80 |
| Lowest | 16.42 | 15.02 | 17.22 |

TABLE 2

Bacterial Susceptibility Data, Amikacin Cefepime, Batch No. RTA02 Amikacin Cefepime Combination on *Klebsiella pneumoniae*

| Concentration | Cefepime Zone (mm) | Amikacin Zone (mm) | Combination Zone (mm) |
| --- | --- | --- | --- |
| Highest | 36.02 | 34.98 | 36.62 |
| High | 32.35 | 31.25 | 33.78 |
| Low | 31.96 | 31.02 | 32.00 |
| Lowest | 30.83 | 29.98 | 31.56 |

TABLE 3

Bacterial Susceptibility Data, Amikacin Cefepime Batch No. RTA02 Amikacin Cefepime Combination on *Streptococcus pneumoniae*

| Concentration | Cefepime Zone (mm) | Amikacin Zone (mm) | Combination Zone (mm) |
| --- | --- | --- | --- |
| Highest | 30.32 | 26.58 | 32.54 |
| High | 28.10 | 24.28 | 30.12 |
| Low | 23.02 | 18.34 | 23.27 |
| Lowest | 19.54 | 12.32 | 21.66 |

TABLE 4

Bacterial Susceptibility Data, Amikacin Cefepime Batch No. RTA02 Amikacin Cefepime Combination on *Enterococcus faecalis*

| Concentration | Cefepime Zone (mm) | Amikacin Zone (mm) | Combination Zone (mm) |
| --- | --- | --- | --- |
| Highest | 28.98 | 27.29 | 30.04 |
| High | 25.52 | 23.24 | 25.97 |
| Low | 19.92 | 17.97 | 20.51 |
| Lowest | 12.65 | 08.05 | 16.98 |

TABLE 5

Bacterial Susceptibility Data, Amikacin Cefepime Batch No. RTA02 Amikacin Cefepime Combination on *Pseudomonas auriginosa*

| Concentration | Cefepime Zone (mm) | Amikacin Zone (mm) | Combination Zone (mm) |
| --- | --- | --- | --- |
| Highest | 30.94 | 26.93 | 31.06 |
| High | 27.56 | 21.81 | 29.10 |
| Low | 18.81 | 16.05 | 20.46 |
| Lowest | 12.08 | 09.81 | 14.99 |

TABLE 6

Bacterial Susceptibility Data, Amikacin Cefepime Batch No. RTA02 Amikacin Cefepime Combination on *Staphylococcus aureus*

| Concentration | Cefepime Zone (mm) | Amikacin Zone (mm) | Combination Zone (mm) |
| --- | --- | --- | --- |
| Highest | 31.06 | 28.92 | 32.80 |
| High | 28.44 | 24.42 | 30.08 |
| Low | 21.18 | 18.79 | 23.27 |
| Lowest | 16.24 | 10.09 | 17.41 |

TABLE 7

Survival Data, Amikacin Cefepime Batch No. RTA02
Swiss Albino Mice

| | | | Group | | | |
|---|---|---|---|---|---|---|
| | Control | X | 2X | 10X | 20X | 30X |
| | | | | Dose | | |
| Day | Diluent | 0.9 mg/20 g | 1.8 mg/20 g | 9.0 mg/20 g | 18.0 mg/20 g | 27.0 mg/20 g |
| | | | No. of surviving mice/Initial no. of mice | | | |
| 0 | 6 of 6 | 6 of 6 | 6 of 6 | 6 of 6 | 6 of 6 | 6 of 6 |
| 1 | 6 of 6 | 6 of 6 | 6 of 6 | 6 of 6 | 6 of 6 | 6 of 6 |
| 2 | 6 of 6 | 6 of 6 | 6 of 6 | 6 of 6 | 6 of 6 | 6 of 6 |
| 3 | 6 of 6 | 6 of 6 | 6 of 6 | 6 of 6 | 6 of 6 | 6 of 6 |
| 4 | 6 of 6 | 6 of 6 | 6 of 6 | 6 of 6 | 6 of 6 | 6 of 6 |
| 5 | 6 of 6 | 6 of 6 | 6 of 6 | 6 of 6 | 6 of 6 | 6 of 6 |
| 6 | 6 of 6 | 6 of 6 | 6 of 6 | 6 of 6 | 6 of 6 | 5 of 6 |
| 7 | 6 of 6 | 6 of 6 | 6 of 6 | 6 of 6 | 6 of 6 | 5 of 6 |

TABLE 8

Ratio Determining Studies showing Bacterial Lytic Zone

| Amikacin:Cefepime Ratio | *Klebsiella pneumoniae* (mm) | *Streptococcus pneumoniae* | *Enterococcus faecalis* | *Pseudomonas auriginosa* | *Staphylococcus aureus* | *E. coli* (mm) |
|---|---|---|---|---|---|---|
| 1:1 | 26 | 23 | 23 | 21 | 24 | 26 |
| 1:2 | 29 | 25 | 27 | 26 | 26 | 25 |
| 1:3 | 32 | 31 | 29 | 29 | 30 | 28 |
| 1:4 | 35 | 32 | 31 | 31 | 33 | 30 |
| 4:1 | 34 | 27 | 26 | 30 | 32 | 29 |
| 4:2 | 31 | 23 | 27 | 26 | 25 | 28 |
| 4:3 | 29 | 29 | 29 | 27 | 30 | 27 |

TABLE 9

Acute Toxicity Data
Amikacin Cefepime, Batch No. RTA02
Animal Behavior Data

| | | X | 2X | 10X | 20X | 30X | |
|---|---|---|---|---|---|---|---|
| | | | | Dose | | | |
| Day | Control | 0.9 mg/20 g | 1.8 mg/20 g | 9.0 mg/20 g | 18 mg/20 g | 27 mg/20 g | Remarks |
| 1 Day | Normal Behavior | Normal Behavior | Normal Behavior | Normal Behavior | Normal Behavior | Aggressive | OK |
| 2 Day | Normal Behavior | Normal Behavior | Normal Behavior | Normal Behavior | Normal Behavior | Aggressive | OK |
| 3 Day | Normal Behavior | Normal Behavior | Normal Behavior | Normal Behavior | Normal Behavior | Aggressive | OK |
| 4 Day | Normal Behavior | Normal Behavior | Normal Behavior | Normal Behavior | Normal Behavior | Normal Behavior | OK |
| 5 Day | Normal Behavior | Normal Behavior | Normal Behavior | Normal Behavior | Normal Behavior | Normal Behavior | OK |
| 6 Day | Normal Behavior | Normal Behavior | Normal Behavior | Normal Behavior | Normal Behavior | Normal Behavior | OK |
| 7 Day | Normal Behavior | Normal Behavior | Normal Behavior | Normal Behavior | Normal Behavior | Normal Behavior | OK |

TABLE 10

Acute Toxicity Data
Amikacin Cefepime, Batch No. RTA02
SUMMARY OF BODY WEIGHT (g) for Swiss Albino Mice

| | | | Group | | | |
|---|---|---|---|---|---|---|
| | Control | X | 2X | 10X | 20X | 30X |
| | | | | Dose | | |
| Day | Diluent | 0.9 mg/20 g | 1.8 mg/20 g | 9.0 mg/20 g | 18 mg/20 g | 27 mg/20 g |
| 0 | 20.52 | 20.54 | 20.56 | 20.57 | 20.60 | 20.63 |
| | 6 | 6 | 6 | 6 | 6 | 6 |
| 1 | 20.50 | 20.51 | 20.55 | 20.56 | 20.58 | 20.61 |
| | 6 | 6 | 6 | 6 | 6 | 6 |
| 2 | 20.50 | 20.52 | 21.54 | 21.54 | 21.55 | 21.58 |
| | 6 | 6 | 6 | 6 | 6 | 6 |
| 3 | 20.51 | 20.50 | 20.53 | 20.52 | 20.50 | 20.50 |
| | 6 | 6 | 6 | 6 | 6 | 6 |
| 4 | 20.51 | 20.51 | 20.53 | 20.48 | 20.47 | 20.39 |
| | 6 | 6 | 6 | 6 | 6 | 6 |
| 5 | 20.45 | 20.44 | 20.41 | 20.39 | 20.36 | 20.33 |
| | 6 | 6 | 6 | 6 | 6 | 6 |
| 6 | 20.44 | 20.43 | 20.41 | 20.37 | 20.31 | 20.27 |
| | 6 | 6 | 6 | 6 | 6 | 5 |
| 7 | 20.43 | 20.43 | 20.39 | 20.37 | 20.26 | 20.16 |
| | 6 | 6 | 6 | 6 | 6 | 5 |

TABLE 11

Average cost comaprison of Prior art v/s invention

| Prior art | Invention | Cost Saved |
|---|---|---|
| Average hospitalization time 13 days @ Rs-1000/day = Rs-13000/- | Average hospitalization time 9 days @ Rs-1000/day = Rs-9000/- | Rs-4000/- per hospital admission |
| Average cost of Cefepime 2 g @250 bd for 13 days and Amikacin 500 mg @65 bd for 13 days = 250 × 2 × 13 = Rs-6500/- + 65 × 2 × 13 = Rs-1690/- Total cost = Rs-8190/- | Average cost of Cefepime Amikacin @350 bd for 9 days = 350 × 2 × 9 = Rs-6300/- Total cost = Rs- 6300/- | Rs-1890/- per treatment cost |

TABLE 12

STABILITY DATA
Generic name of product: Cefepime & Amikacin for Inj.
Batch No.: RTA02
Date of Mfg.: October 2004 Date of Exp.: September 2006 Date of initiating: 29.10.2004
Packaging: glass vial

| | | | | | | | | (a) Assay | |
|---|---|---|---|---|---|---|---|---|---|
| Period (mo) | Storage Conditions | Description | Identification | Particulate matter | pH (3.0-6.0) | BET | Sterility | 90% to 110% of labelled amount of Cefepime | 90% to 110% of labelled amount of Amicacin |
| Initial | — | A cream colored powder | Passes test | Passes test | 4.52 | Passes test | Passes test | 100.1 | 99.8 |
| 1. | 40° C./75% RH | A dark cream colored powder | " | " | 4.48 | " | " | 99.5 | 99.3 |
| 2. | 40° C./75% RH | A cream colored powder with yellowish tinge | " | " | 4.41 | " | " | 99.0 | 98.5 |

TABLE 12-continued

STABILITY DATA
Generic name of product: Cefepime & Amikacin for Inj.
Batch No.: RTA02
Date of Mfg.: October 2004 Date of Exp.: September 2006 Date of initiating: 29.10.2004
Packaging: glass vial

| Period (mo) | Storage Conditions | Description | Identification | Particulate matter | pH (3.0-6.0) | BET | Sterility | (a) Assay 90% to 110% of labelled amount of Cefepime | 90% to 110% of labelled amount of Amicacin |
|---|---|---|---|---|---|---|---|---|---|
| 3. | 40° C./75% RH | A light yellow colored powder | " | " | 4.31 | " | " | 98.2 | 97.6 |
| 6. | 40° C./75% RH | A light yellow colored powder | " | " | 3.91 | " | " | 97.4 | 96.9 |

REMARKS:
1. All procedure carried out as per STP.
2. Product as stable for 6 month at 40°/75% RH While the above description contains many specificities, these should not be construed as limitations in the scope of the invention but as exemplifications of embodiments thereof. Many other variations are possible. Accordingly, the scope of the invention should be determined not by the embodiments illustrated, but by the appended claims and their legal equivalents.

I claim:

1. An antibiotic composition suitable for parenteral injection, comprising:
    a) A first antibiotic which is a protein synthesis inhibiting antibiotic, wherein said protein synthesis inhibiting antibiotic is an aminoglycoside selected from the group consisting of gentamycin, amikacin, tobramycin and pharmaceutically acceptable salts thereof;
    b) A second antibiotic which is a non-protein synthesis inhibiting antibiotic, wherein said non-protein synthesis inhibiting antibiotic is a beta lactam cephalosporin selected from the group consisting of cefepime, and pharmaceutically acceptable salts thereof; and
    c) L-arginine, wherein the L-arginine is provided in an amount effective to stabilize the first antibiotic with the second antibiotic in the composition,
    wherein said first antibiotic and said second antibiotic are present in a weight ratio of 1:5 to 5:1;
    wherein said L-arginine is present in a range of 35% to 75% w/w of combined weight of said first antibiotic and said second antibiotic; and
    wherein said antibiotic composition is present in a reconstitutable dry powder form suitable for reconstitution and for concurrent parenteral administration.

2. The composition of claim 1, wherein the dry powder is sterilized.

3. The composition of claim 1, wherein the first antibiotic is amikacin, amikacin sulphate, or pharmaceutically acceptable salts thereof.

4. The composition of claim 3, wherein the second antibiotic is cefepime, a pharmaceutically acceptable salt of cefepime, or a combination thereof, further wherein said amikacin, amikacin sulphate, or pharmaceutically acceptable salt thereof and said cefepime or pharmaceutically acceptable salt thereof form a precipitate in absence of the L-arginine when provided in combination in a single dose form at the listed weight ratio.

5. The composition of claim 2, wherein the sterilized dry powder is packed and sealed in a sterile container selected from the group consisting of a vial, an ampoule, a syringe, a packet, a pouch and an auto-injector vessel under blanket of inert gas.

6. The composition of claim 5, wherein an interior space of the container comprises a fill volume occupied by the antibiotic composition in said a reconstituted form and a head space volume occupied aseptically by an inert gas limited microatmosphere, the inert gas being not more than 5% of the head space volume, and wherein ratio of said fill volume to said head space volume is not less than 1:1.

7. The antibiotic composition of claim 1, wherein:
    said first antibiotic is amikacin or a pharmaceutically acceptable salt thereof;
    said second antibiotic is cefepime or a pharmaceutically acceptable salt thereof;
    said first antibiotic and said second antibiotic is present in a weight ratio of 1:4.

8. The antibiotic composition of claim 7, wherein
    a) said amikacin or pharmaceutically acceptable salt thereof is present in an amount from about 50 mg to about 75 mg, calculated as amikacin free acid;
    b) said cefepime or pharmaceutically acceptable salt thereof is present in an amount from about 250 mg to about 500 mg, calculated as cefepime free acid; and
    c) the L-arginine is present in an amount from about 75 mg to about 150 mg, wherein said antibiotic composition is reconstituted with 3 ml of water for injection.

9. The antibiotic composition of claim 7, wherein
    a) said amikacin or pharmaceutically acceptable salt thereof is present in an amount from about 100 mg to about 150 mg, calculated as amikacin free acid;
    b) said cefepime or pharmaceutically acceptable salt thereof is present in an amount from about 500 mg to 1000 mg, calculated as cefepime free acid; and
    c) the L-arginine is present in an amount from about 150 mg to about 300 mg, wherein said antibiotic composition is reconstituted with 5 ml of water for injection.

10. The antibiotic composition of claim 7, wherein
    a) said amikacin or pharmaceutically acceptable salt thereof is present in an amount from about 400 mg to about 600 mg, calculated as amikacin free acid;

b) said cefepime or pharmaceutically acceptable salt thereof is present in an amount from about 2000 mg to about 4000 mg, calculated as cefepime free acid; and
c) the L-arginine is present in an amount from about 600 mg to about 1200 mg, wherein said antibiotic composition is reconstituted with 20 ml of water for injection.

11. The antibiotic composition of claim 7, wherein:

said amikacin or pharmaceutically acceptable salt thereof is present in an amount from about 200 mg to about 300 mg, calculated as amikacin free acid;

said cefepime or pharmaceutically acceptable salt thereof is present in an amount from about 1000 mg to about 2000 mg, calculated as cefepime free acid; and the L-arginine is present in an amount from about 300 mg to about 600 mg, wherein said antibiotic composition is reconstituted with 10 ml of water for injection.

12. A method of treating bacterial infection in mammals, comprising
a) reconstituting the dry power composition of claim 1, and
b) parenterally administering the reconstituted composition to a patient in need of treatment thereof.

13. A process of preparing the antibiotic combination of the composition of claim 1, comprising
a) blending of the first antibiotic and the second antibiotic under sterile conditions;
b) adding the L-arginine to the mixture of step (a);
c) blending the mixture of step (b) for a period ranging from about 1 hour to about 4 hours;
d) proportioning the mixture of step (c) into a container; and
e) capping aseptically the container with pre-post inert gassing.

* * * * *